United States Patent
Nakai et al.

(10) Patent No.: US 11,304,658 B2
(45) Date of Patent: Apr. 19, 2022

(54) METHOD FOR DIAGNOSING CEREBROSPINAL FLUID HYPOVOLEMIA

(71) Applicant: NATIONAL UNIVERSITY CORPORATION KOCHI UNIVERSITY, Kochi (JP)

(72) Inventors: Eiichi Nakai, Kochi (JP); Tetsuya Ueba, Kochi (JP)

(73) Assignee: National University Corporation Kochi University, Kochi (JP)

( * ) Notice: Subject to any disclaimer, the term of this patent is extended or adjusted under 35 U.S.C. 154(b) by 68 days.

(21) Appl. No.: 16/536,664

(22) Filed: Aug. 9, 2019

(65) Prior Publication Data
US 2021/0038152 A1 Feb. 11, 2021

(51) Int. Cl.
*A61B 5/00* (2006.01)
*A61M 31/00* (2006.01)

(52) U.S. Cl.
CPC .......... *A61B 5/4884* (2013.01); *A61B 5/4064* (2013.01); *A61M 31/00* (2013.01); *A61M 2202/0468* (2013.01); *A61M 2210/0693* (2013.01)

(58) Field of Classification Search
CPC ... A61B 17/3401; A61B 5/4088; A61B 5/032; A61B 10/025; A61B 17/3415; A61B 2090/034; A61B 2090/065; A61B 5/055; A61B 5/065; A61B 5/742; A61B 2576/026; A61B 6/501; A61B 5/00; A61B 6/032; A61B 5/031; A61B 5/1116; A61B 5/4076; A61B 5/4561
See application file for complete search history.

(56) References Cited

U.S. PATENT DOCUMENTS

| | | | |
|---|---|---|---|
| 9,907,864 B1 | 3/2018 | Nakai | |
| 2002/0179095 A1* | 12/2002 | Almazov | ............. A61B 5/4824 128/898 |

OTHER PUBLICATIONS

Binder et al. (International Saline Infusion in The Treatment of Obtundation Associated with Spontaneous Intracranial Hypotension: Technical Case Report, Neurosurgery 51:830-837, 2002) (Year: 2002).*
Thomas et al. (Radionuclide Cisternography in Detecting Cerebrospinal Fluid Leak in Spontaneous Intracranial Hypotension, Clinical Nuclear Medicine, vol. 34, No. 7, Jul. 2009). (Year: 2009).*
Epidural space definition (back pain and neck pain medical glossery, accessed Oct. 20, 2021). (Year: 2021).*
Angelo Franzini et al., "Intracranial Spontaneous Hypotension Associated with CSF Cervical Leakage Successfully Treated by Lumbar Epidural Blood Patch", Acta Neurochir, 152, pp. 1997-1999 (2010).
Ansaar Rai et al., "Epidural Blood Patch at C2: Diagnosis and Treatment of Spontaneous Intracranial Hypotension", AJNR Am J Neuroradial, 6, pp. 2663-2666 (2005).
Bobby Mehta, Jordan Tarshis, "Repeated Large-Volume Epidural Blood Patches for the Treatment of Spontaneous Intracranial Hypotension", Can J Anesth, 56, pp. 609-613 (2009).
Keisuke Watanabe et al., "Fluoroscopically Guided Epidural Blood Patch with Subsequent Spinal CT Scans in the Treatment of Spontaneous Cerebrospinal Fluid Hypovolemia", J Neurosurg, 114, pp. 1731-1735 (2011).
Damita L. Thomas et al., "Radionuclide Cisternography, in Detecting Cerebrospinal Fluid Leak in Spontaneous Intracranial Hypotension", Clinical Nuclear Medicine, 34(7), pp. 410-416 (2009).

* cited by examiner

*Primary Examiner* — Melissa S Mercier
(74) *Attorney, Agent, or Firm* — Wenderoth, Lind & Ponack, L.L.P.

(57) ABSTRACT

The method for diagnosing cerebrospinal fluid hypovolemia includes injecting saline into a subdural space of a subject in a decubitus position, raising an upper body of the subject, and then determining whether the subject has headache or not, or headache of the subject is relieved or not.

6 Claims, No Drawings

METHOD FOR DIAGNOSING CEREBROSPINAL FLUID HYPOVOLEMIA

BACKGROUND OF THE INVENTION

Field of the Invention

One or more embodiments of the present invention relate to a method for effectively diagnosing cerebrospinal fluid hypovolemia.

Description of the Related Art

Cerebrospinal fluid hypovolemia (CSFH) is caused by decreasing an amount of cerebrospinal fluid (CSF) due to some causes. A CSFH patient presents with headache, neck pain, dizziness, tinnitus, fatigue or the like as a symptom. In particular, orthostatic headache is mainly confirmed in CSFH. In general, CSFH is considered to be treatable; however, CSFH has a problem that it is difficult to diagnose CSFH. Specifically, it is exemplified as a main cause of CSFH that CSF, which fills cerebrospinal cavum around brain and spinal cord, persistently or intermittently leaks out due to high impact on body or head by traffic accident or the like. However the causal relationship between the cause and symptom is hardly specified, since it takes time to experience a symptom from the cause arises.

In order to treat CSFH, it is very important to specify a leakage part of CSF. Specifically, epidural blood patch is effective for treating CSFH caused by a leakage of CSF (Non-patent documents 1 to 4). In epidural blood patch, autologous blood is injected into extradural space at a leakage part of CSF and coagulated to patch the leakage part. It is however difficult to diagnose CSFH before epidural blood patch.

When a patient is suspected to have CSFH, firstly, a spine image is generally taken by magnetic resonance imaging (MRI). MRI is safe, since it is not needed in MRI to use a medicine. It is however difficult by MRI to determine whether CSF leaks or not and to specify the leakage part. Then, CSF pressure is measured by lumbar puncture. If CSF pressure is lower than 6 cm $H_2O$, a patient is diagnosed with CSFH. The value of CSF pressure, however, changes due to various causes. In addition, CSF pressure during normal time and a threshold of CSF pressure of CSFH are different depending on individual. There are, therefore, false negative patients having CSF pressure of lower than 6 cm $H_2O$, and CSF pressure measurement is not valuable in CSFH diagnosis.

When it is confirmed that CSF is leaked in a subject, the subject is diagnosed with CSFH. In order to specify a leakage part of CSF, computed tomography (CT) myelography and radio isotope (RI) cerebral scintigraphy are generally carried out (Non-patent Document 5). In CT myelography, a contrast medium is injected into subdural space and a diffusion image of the injected contrast medium is taken using X-ray. In RI cerebral scintigraphy, RI is injected into subdural space and an image of a spinae is taken using a gamma camera, by which radiation dose can be recognized. In addition, MRI myelography with using a contrast medium is carried out in some cases. However, as described above, it is very difficult to specify the leakage part, since a leakage amount of CSF is small. In particular, when the leakage part is in upper part of a spine, it is more difficult to specify the leakage part, since a contrast medium and RI are injected by lumbar puncture and the concentrations thereof become lower in upper part of a spine. It is therefore needed to take images multiple times in the diagnosis using the above-described means. Nevertheless, a leakage part of CSF cannot be specified by the above-described means in many cases. According to certain statistics, the rate of specifying a leakage part of CSF by the above-described means is only 10 to 20%. In addition, the above-described means have problems of a side effect by a contrast medium and radiation exposure by RI.

The inventor have developed a method for specifying a leakage part of cerebrospinal fluid in a cerebrospinal fluid hypovolemia patient (Patent document 1). In this method, saline is injected into a subdural space of a spine of a cerebrospinal fluid hypovolemia patient, and the cerebrospinal fluid or the injected saline leaked from a dura mater of the spine is detected to specify the leakage part of the cerebrospinal fluid.

Patent document 1: U.S. Pat. No. 9,907,864 B1
Non-patent document 1: Angelo Franzini et al., Acta Neurochir, 152, pp. 1997-1999 (2010)
Non-patent document 2: Ansaar Rai et al., AJNR Am J Neuroradial, 26, pp. 2663-2666 (2005)
Non-patent document 3: Bobby Mehta, Jordan Tarshis, Can J Anesth, 56, pp. 609-613 (2009)
Non-patent document 4: Keisuke Watanabe et al., J Neurosurg, 114, pp. 1731-1735 (2011)
Non-patent document 5: Damita L. Thomas et al., Clinical Nuclear Medicine, 34(7), pp. 410-416 (2009)

SUMMARY OF THE INVENTION

As described above, it is difficult to diagnose cerebrospinal fluid hypovolemia.

One or more embodiments of the present invention provide a method for a method for effectively diagnosing cerebrospinal fluid hypovolemia.

The inventor found that cerebrospinal fluid hypovolemia can be effectively diagnosed without difficulty by taking into consideration the fact that orthostatic headache or the like resulting from cerebrospinal fluid hypovolemia is improved by supplementing decreased cerebrospinal fluid with saline.

Hereinafter, one or more embodiments of the present invention are described.

[1] A method for diagnosing cerebrospinal fluid hypovolemia, comprising the steps of:
injecting saline into a subdural space of a subject in a decubitus position,
raising an upper body of the subject, and
then determining whether the subject has headache or not, or headache of the subject is relieved or not.

[2] The method according to the above [1], wherein an upper body of the subject is raised and then the subject is put in the decubitus position for saline injection.

[3] The method according to the above [2], wherein the upper body was kept to be raised until orthostatic headache is caused before injecting saline.

[4] The method according to the above [2], wherein the subject is raised and then the subject is put in the decubitus position for saline injection.

[5] The method according to the above [1], wherein an amount of the saline is 5 mL or more and 15 mL or less.

[6] The method according to the above [1], wherein the subject is raised after saline is injected.

One or more embodiments of the present invention is very safe, since saline is used but a contrast medium and RI are not used. In addition, according to one or more embodiments of the present invention, cerebrospinal fluid hypovolemia can be diagnosed by very simple procedure, specifically by injecting saline into a subdural space of a subject in a decubitus position. Since cerebrospinal fluid hypovolemia can be effectively diagnosed according to one or more embodiments of the present invention, a subsequent treatment is also effective.

DESCRIPTION OF THE PREFERRED EMBODIMENTS

Hereinafter, each step of one or more embodiments of the present invention method is described. Hereinafter, cerebrospinal fluid is abbreviated to "CSF" and cerebrospinal fluid hypovolemia is abbreviated to "CSFH".

1. Saline Injection Step

In the present step, saline is injected into a subdural space of a subject in a decubitus position.

The "subject" is not particularly restricted as long as the subject is suspected to have CSFH. CSFH is a disease in which various symptoms such as headache, dizziness, neck pain, tinnitus, decreased visual acuity, general fatigue are displayed due to the decrease of CSF filling around the brain and spinal cord. A CSFH patient mainly has orthostatic headache. Orthostatic headache is a kind of headache in which the exacerbation of headache in a standing position for several minutes and the improvement or disappearance in a decubitus position are shown.

In one or more embodiments of the present invention, the term "spine" does not mean a specific individual vertebra but includes all of vertebrae and means so-called spinal column. For example, saline is injected into a subdural space of a spine mainly by lumbar puncture in one or more embodiments of the present invention as described later and a dura mater crack which is a cause of CSFH may be inside of the vertebrae into which saline is injected in some cases; however, the dura mater crack is rather inside of another vertebrae in many cases.

In one or more embodiments of the present invention, the term "saline" means a sodium chloride aqueous solution which is isotonic or nearly isotonic with a body fluid. For example, approximately 0.9 w/v % sodium chloride aqueous solution can be used as saline. Saline may contain a component other than sodium chloride as long as the saline is isotonic or nearly isotonic with a body fluid. Such a component other than sodium chloride is exemplified by a sugar such as glucose; a potassium salt; a salt of group 2 element, such as a calcium salt and a magnesium salt; an inorganic acid salt such as a chloride salt, a hydrogencarbonate salt and a dihydrogen phosphate salt; and an organic acid salt such as an acetate salt and a lactate salt. In addition, commercially available artificial cerebrospinal fluid and Ringer's solution may be used as saline.

An amount of saline to be injected into a subdural space of a spine may be appropriately adjusted. When an amount of injected saline exceeds a certain threshold amount, the subject's symptom may be improved more easily even if only temporarily. In addition, CSFH is caused by the decrease of amount and pressure of CSF; therefore, even when saline is injected in a large amount, harmful is less. However, when the injected amount is excessively large, a harmful effect may be possibly exerted due to an excessive increase of CSF pressure and leaked CSF amount. For example, an amount of saline to be injected may be adjusted to 5 mL or more and 15 mL or less.

Saline is injected into a subdural space of a subject in a decubitus position. Saline is a sodium chloride aqueous solution having an osmotic pressure which is the same as or approximately similar to a body fluid, and in general, about 0.9 w/v % sodium chloride aqueous solution having pH of from 4.5 through 8.0. A decubitus position means a posture in a recumbent state. In general, a decubitus position is mainly a supine position, prone position or lateral position; however, in one or more embodiments of the present invention, a decubitus position is a prone position and lateral position from a standpoint of ease of saline injection. As the means for the injection of saline, general lumbar puncture may be employed.

It is preferred that the upper body of the subject is raised before saline is injected into the subject. Orthostatic headache, which is a main symptom of CSFH, is caused in a standing position and improved in a decubitus position. In addition, when orthostatic headache is caused by the decrease of CSF pressure, orthostatic headache is improved by injecting saline. It therefore becomes easy to diagnose whether a subject has CSFH or not by raising the upper body of the subject before injecting saline so that the subject easily has headache or orthostatic headache is easily caused. A CSFH patient is considered to have headache by raising the upper body of the patient so that CSF pressure is decreased, and the time from raising the patient's upper body to the onset of headache varies depending on the patient. It is therefore preferred that the upper body of a subject is raised until orthostatic headache is caused before injecting saline into the subject; as a result, the time from raising the patient's upper body to the onset of headache can be specified. In one or more embodiments of the present invention, the phrase "raising an upper body of a subject" means that the upper body of the subject becomes vertical or approximately vertical and the subject may be standing or in a sitting position. It is however preferred to have the subject standing, since orthostatic headache is caused more easily.

Saline may be injected at a time or in two or more installments. For example, saline may be injected in two or more installments in order not to excessively increase CSF pressure while CSF pressure is measured.

2. Raising Step

In the present step, an upper body of a subject is raised after saline is injected into a subdural space of the subject in a decubitus position.

Orthostatic headache is characteristically observed in a CSFH patient. In the present step, the upper body of the subject into whom saline has been injected is raised in a similar condition to a condition that a CSFH patient has orthostatic headache to whom saline has been not injected. Specifically, after injecting saline into a subdural space of a subject, it is preferred that the upper body of the subject is raised within 5 minutes. Orthostatic headache is generally relieved by laying a patient, but when the time from saline injection to raising the subject's upper body is 5 minutes or less, it is easy to determine whether the reason for an improvement of orthostatic headache is saline injection or not. The time may be not more than 4 minutes, not more than 3 minutes, not more than 2 minutes or not more than 1 minute. On the one hand, in the case where an upper body of a CSFH patient is raised in a hurry, the patient may suffer pain; therefore, the time from saline injection to raising the subject's upper body may be 30 seconds or more.

3. Diagnosis Step

In the present step, after raising the upper body of the subject, it is determined whether the subject has headache or not, or headache of the subject is relieved or not.

Orthostatic headache is characteristically observed in a CSFH patient, and CSFH is caused by lack of CSF due to leakage or the like of CSF. Accordingly, when saline is injected into a subdural space of a CSFH patient as a subject, symptoms are improved by injecting saline, and in particular, orthostatic headache, which is a main symptom in CSFH, is eliminated or relieved. On the one hand, in the case where a subject is suspected to have CSFH due to orthostatic headache but practically does not have CSFH, even when saline is injected into the subject, orthostatic headache will not be relieved. As a result, when a subject does not have headache or headache is relieved after saline is injected into a subdural space of the subject in a decubitus position and the upper body of the subject is raised, the subject is diagnosed with CSFH; and when the subject has headache or headache is not relieved, the subject is not diagnosed with CSFH. In addition, a symptomatic state which is alleviated by injecting saline is thought of as a a symptomatic state which is alleviated by a CSFH treatment to stop the leakage of CSF.

As described above, the time from raising the upper body to having headache is different depending on a patient; but when the time from raising the upper body to having headache is measured before injecting saline, CSFH can be diagnosed more easily by determining whether the subject has headache or not approximately at the measured time.

4. Treatment Step

In the present step, when the subject is diagnosed with CSFH, the subject is treated. Specifically, first, a leakage part of CSF is specified. For example, a leakage part of CSF may be specified by a general method such as CT myelography and RI cerebral scintigraphy or a method which was developed by the inventor and which is described in U.S. Pat. No. 9,907,864.

Then, epidural blood patch is carried out at the leakage part to caulk the leakage part. Epidural blood patch is a method to caulk a leakage part of CSF by injecting autologous blood into extradural space at the leakage part and coagulating the injected blood.

Epidural blood patch may be carried out in an ordinary condition. Specifically, about 30 mL of blood in males and about 20 mL of blood in females is collected from a patient's vein, and the collected blood is injected between the dura mater at the specified leakage part of CSF and the outside adipose tissue. Epidural blood patch may be carried out from one time to three times or so while a patient's condition is monitored.

EXAMPLES

Hereinafter, one or more embodiments of the present invention is described in more detail with Examples. However, the present invention is not restricted to the following Examples in any way, and it is possible to work the present invention according to the Examples with an additional appropriate change within the range of the above descriptions and the following descriptions. Such a changed embodiment is also included in the technical scope of the present invention.

The abbreviated expressions used in the following disclosure are described as follows.
CSF: cerebrospinal fluid
CSFH: cerebrospinal fluid hypovolemia
EBP: epidural blood patch Example 1

(1) Subject

The patient who is suspected to have CSFH due to orthostatic headache as a main complaint is selected as a subject.

(2) Diagnosis

A 22 G lumbar puncture needle is punctured between the fourth lumbar and the fifth lumbar of the subject in a lateral position in accordance with Jacoby line, and CSF pressure is measured. Then, 10 mL of saline is injected. It is confirmed that there is no particular problem, and immediately after the needle is pulled out, the subject is allowed to stand within 5 minutes from needle removal at the latest. After raising the subject, the symptoms are observed.

(3) Determination of Leaking Position

After 20 mL of saline is injected into the subdural space of the subject, the leakage part of CSF is specified by MRI scans. In addition, the leakage part is also confirmed by CT myelography and RI cerebral scintigraphy.

(4) Treatment

EBP is conducted by injecting 20 mL or 30 mL of autologous blood of the subject at the specified leakage part.

The invention claimed is:

1. A method for diagnosing cerebrospinal fluid hypovolemia, comprising the steps of:
   injecting saline into a subdural space of a subject in a decubitus position, the subject having an orthostatic headache,
   raising an upper body of the subject within 5 minutes after injecting the saline into the subdural space of the subject in the decubitus position, and
   then determining whether the orthostatic headache in the subject has been eliminated or relieved or not,
   wherein the subject is diagnosed as having cerebrospinal fluid hypovolemia in the case where the orthostatic headache is eliminated or relieved, and the subject is diagnosed as not having cerebrospinal fluid hypovolemia in the case where the orthostatic headache is not eliminated or relieved.

2. The method according to claim 1, wherein, prior to the step of injecting the saline into the subdural space of the subject in the decubitus position, the subject is sitting with the upper body of the subject raised.

3. The method according to claim 2, wherein the upper body is kept raised until the orthostatic headache is caused, prior to the step of injecting the saline into the subdural space of the subject in the decubitus position.

4. The method according to claim 1, wherein, prior to the step of injecting the saline into the subdural space of the subject in the decubitus position, the subject is standing.

5. The method according to claim 1, wherein an amount of the saline is 5 mL or more and 15 mL or less.

6. The method according to claim 4, wherein the subject is kept standing until the orthostatic headache is caused, prior to the step of injecting the saline into the subdural space of the subject in the decubitus position.

* * * * *